United States Patent

Mori

(10) Patent No.: US 9,167,987 B2
(45) Date of Patent: Oct. 27, 2015

(54) MAGNETIC RESONANCE IMAGING APPARATUS AND MAGNETIC RESONANCE IMAGING METHOD

(75) Inventor: Akio Mori, Otawara (JP)

(73) Assignees: KABUSHIKI KAISHA TOSHIBA, Tokyo (JP); TOSHIBA MEDICAL SYSTEMS CORPORATION, Tochigi-Ken (JP)

(*) Notice: Subject to any disclaimer, the term of this patent is extended or adjusted under 35 U.S.C. 154(b) by 234 days.

(21) Appl. No.: 12/700,207

(22) Filed: Feb. 4, 2010

(65) Prior Publication Data

US 2010/0198050 A1  Aug. 5, 2010

(30) Foreign Application Priority Data

Feb. 5, 2009 (JP) .................. 2009-025286
Dec. 14, 2009 (JP) .................. 2009-283205

(51) Int. Cl.
*A61B 5/055* (2006.01)
*G01R 33/567* (2006.01)

(52) U.S. Cl.
CPC ............ *A61B 5/055* (2013.01); *G01R 33/5673* (2013.01)

(58) Field of Classification Search
CPC .................... A61B 5/055; G01R 33/5673
See application file for complete search history.

(56) References Cited

U.S. PATENT DOCUMENTS

| | | | |
|---|---|---|---|
| 4,903,704 A * | 2/1990 | Van Eggermond et al. | 600/413 |
| 5,000,182 A * | 3/1991 | Hinks | 600/413 |
| 5,218,532 A * | 6/1993 | Mori | 600/410 |
| 6,424,153 B1 * | 7/2002 | Liu et al. | 324/309 |
| 6,438,405 B1 * | 8/2002 | Mooney et al. | 600/427 |
| 2005/0065430 A1 * | 3/2005 | Wiethoff et al. | 600/413 |
| 2006/0183999 A1 * | 8/2006 | Lorenz et al. | 600/410 |
| 2009/0149768 A1 * | 6/2009 | Sprung | 600/523 |
| 2009/0234218 A1 * | 9/2009 | Washburn et al. | 600/410 |

FOREIGN PATENT DOCUMENTS

| | | |
|---|---|---|
| JP | 8-266502 | 10/1996 |
| JP | 2008-125986 | 6/2008 |

OTHER PUBLICATIONS

Office Action dated Oct. 8, 2013 in JP 2009-283205.

* cited by examiner

*Primary Examiner* — Ruth S Smith
(74) *Attorney, Agent, or Firm* — Nixon & Vanderhye P.C.

(57) ABSTRACT

A magnetic resonance imaging apparatus collects raw data about a subject in a synchronized manner with an electrocardiographic signal of the subject. An Electrocardiogram (ECG) gating unit detects an irregular synchronization interval with respect to the electrocardiographic signal. When the ECG gating unit detects an irregular synchronization interval, a real-time sequencer controls a gradient magnetic-field power source, a transmitting unit, and the like so as to reacquire raw data that is acquired during the irregular synchronization interval.

5 Claims, 13 Drawing Sheets

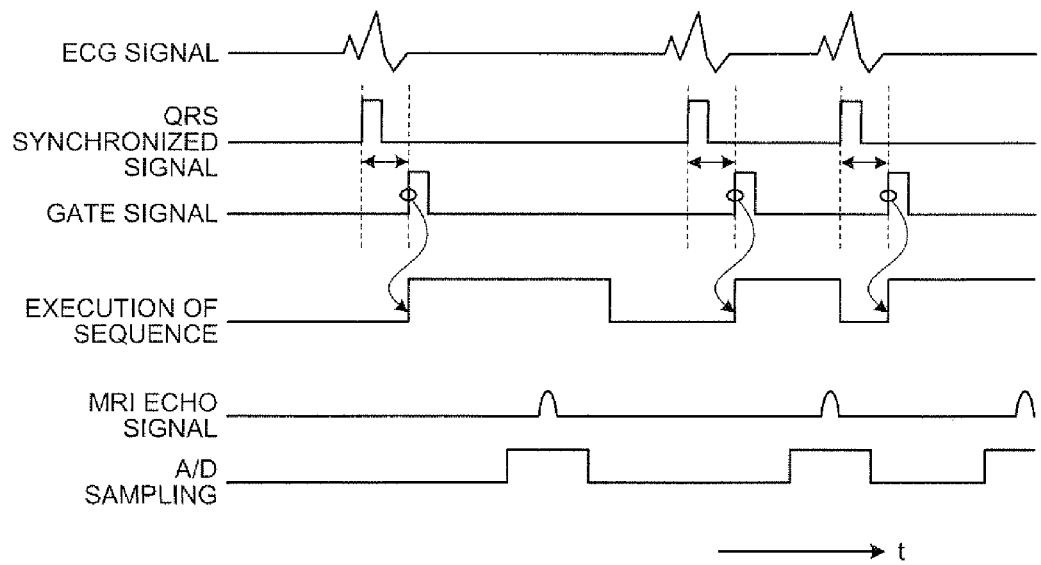
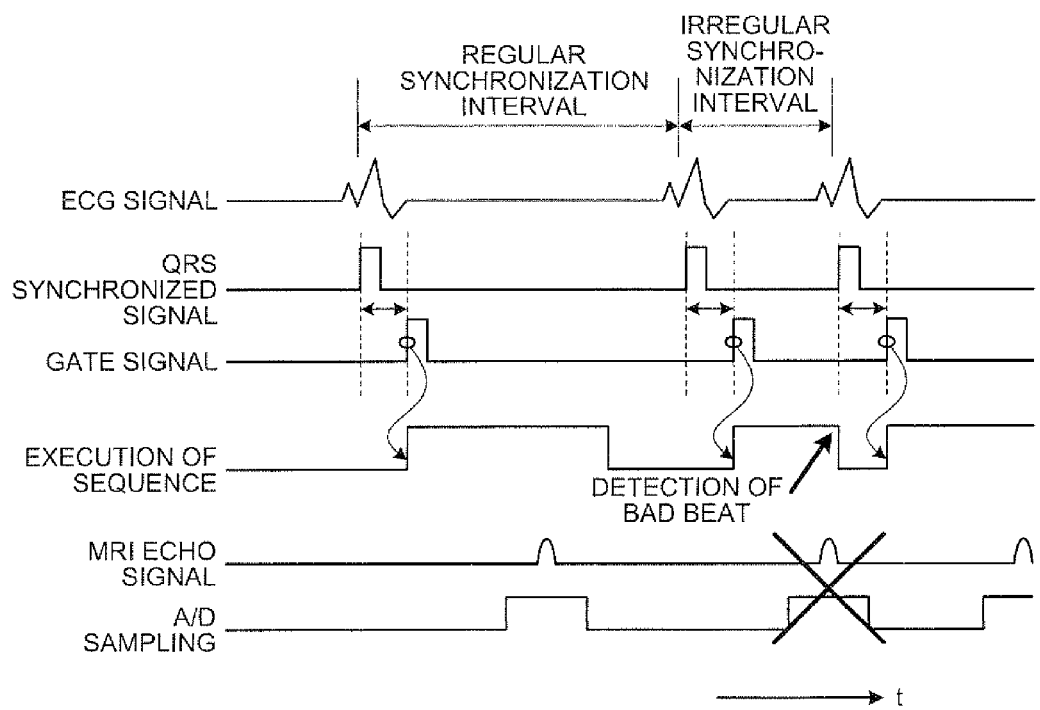

FIG.5

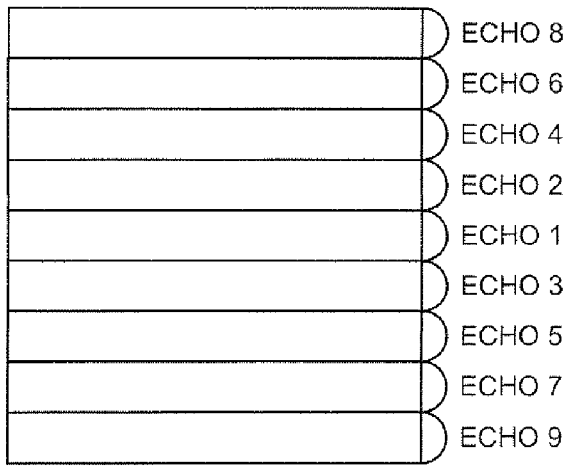

ECHO 8
ECHO 6
ECHO 4
ECHO 2
ECHO 1
ECHO 3
ECHO 5
ECHO 7
ECHO 9

FIG.6

|  | GRADIENT MAGNETIC-FIELD POWER SOURCE | | TRANSMITTING UNIT | | RECEIVING UNIT |  |
|---|---|---|---|---|---|---|
|  | CURRENT STRENGTH | SUPPLY TIMING | RF PULSE STRENGTH | TRANS-MITTING TIMING | RECEIVING TIMING |  |
| TR 1 | STRENGTH 1 | TIMING 1 | STRENGTH 1 | TIMING 1 | TIMING 1 |  |
| TR 2 | STRENGTH 2 | TIMING 2 | STRENGTH 2 | TIMING 2 | TIMING 2 | POINTER |
| TR 3 | STRENGTH 3 | TIMING 3 | STRENGTH 3 | TIMING 3 | TIMING 3 | ⇐ |
| TR 4 | STRENGTH 4 | TIMING 4 | STRENGTH 4 | TIMING 4 | TIMING 4 |  |
| TR 5 | STRENGTH 5 | TIMING 5 | STRENGTH 5 | TIMING 5 | TIMING 5 |  |
| TR 6 | STRENGTH 6 | TIMING 6 | STRENGTH 6 | TIMING 6 | TIMING 6 |  |
| TR 7 | STRENGTH 7 | TIMING 7 | STRENGTH 7 | TIMING 7 | TIMING 7 |  |
| TR 8 | STRENGTH 8 | TIMING 8 | STRENGTH 8 | TIMING 8 | TIMING 8 |  |
| TR 9 | STRENGTH 9 | TIMING 9 | STRENGTH 9 | TIMING 9 | TIMING 9 |  |

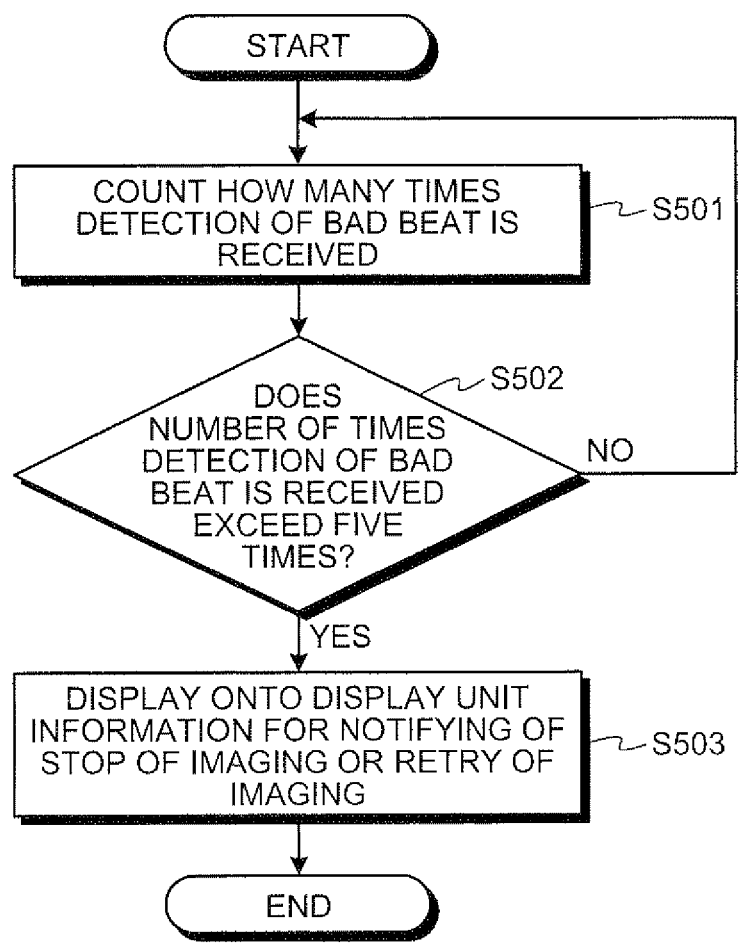

MAGNETIC RESONANCE IMAGING APPARATUS AND MAGNETIC RESONANCE IMAGING METHOD

CROSS-REFERENCE TO RELATED APPLICATIONS

This application is based upon and claims the benefit of priority from the prior Japanese Patent Application No. 2009-25286, filed on Feb. 5, 2009, and No. 2009-283205, filed on Dec. 14, 2009; the entire contents of which are incorporated herein by reference.

BACKGROUND OF THE INVENTION

1. Technical Field

The present invention relates to a magnetic resonance imaging apparatus and a magnetic resonance imaging method.

2. Related Art

Recently, when taking a medical image of a circulatory system, a technique of Electrocardiogram (ECG) gated imaging by which imaging is performed in a synchronized manner with electrocardiographic signals of a subject is used. For example, a technique of ECG gated imaging performed by a magnetic resonance imaging apparatus is disclosed in JP-A 2008-125986 (KOKAI).

However, according to the technique of the ECG gated imaging, when irregularity in the heart beat is sometimes induced by a motion or an irregular pulse of a subject in some cases, a doctor has to read an abnormal image (ghost image) or an image with a phase shift. For this reason, a conventional apparatus includes a configuration that detects an irregular synchronization interval, and when an irregular synchronization interval is detected, ECG gated imaging is stopped, and imaging is performed again from the beginning.

However, such conventional technology described above has a problem that an imaging time becomes long. In other words, according to the conventional technology, although an irregular synchronization interval can be detected, after all, imaging needs to be performed again from the beginning. As a result, collected data is discarded, a long imaging time is wasted, and moreover, retry of imaging from the beginning results in a long time required for imaging, which causes a long time in the imager for the subject.

BRIEF SUMMARY OF EXEMPLARY EMBODIMENTS

According to one aspect of the present exemplary embodiments, a magnetic resonance imaging apparatus includes an acquiring unit that acquires raw data about a subject in a synchronized manner with an electrocardiographic signal of the subject; a detecting unit that detects an irregular synchronization interval with respect to the electrocardiographic signal; and an acquisition control unit that controls the acquiring unit such that when the detecting unit detects an irregular synchronization interval, the acquiring unit reacquires raw data that is acquired during the irregular synchronization interval.

According to another aspect of the present exemplary embodiment, a magnetic resonance imaging method includes acquiring raw data about a subject in a synchronized manner with an electrocardiographic signal of the subject; detecting an irregular synchronization interval with respect to the electrocardiographic signal; and providing control such that when an irregular synchronization interval is detected, raw data that is acquired during the irregular synchronization interval is to be reacquired.

BRIEF DESCRIPTION OF THE DRAWINGS

FIGS. 3 and 4 are Electrocardiogram (ECG) gating timing charts;

FIG. 5 is a schematic diagram for explaining an imaging method;

FIG. 6 is a schematic diagram for explaining sequence information;

FIG. 16 is a flowchart of a process procedure performed by a real-time sequencer.

DETAILED DESCRIPTION OF EXEMPLARY EMBODIMENTS

Exemplary embodiments of a magnetic resonance imaging apparatus (hereinafter, "MRI apparatus") and a magnetic resonance imaging method according to the present invention will be explained below in detail with reference to the accompanying drawings. The present invention is not limited to the following embodiments.

Figure 1:
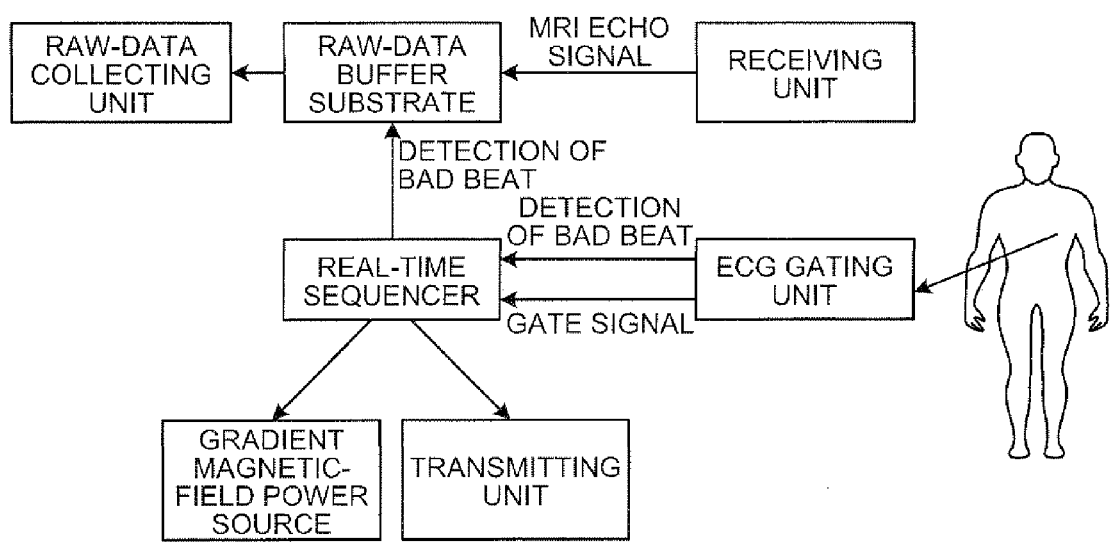
FIG. 1 is a schematic diagram for explaining an outline of a Magnetic Resonance Imaging (MRI) apparatus according to a first embodiment of the present invention.

First of all, an outline of an MRI apparatus according to a first embodiment of the present invention is explained below with reference to FIG. 1. FIG. 1 is a schematic diagram for explaining an outline of the MRI apparatus according to the first embodiment.

As shown in FIG. 1, in the MRI apparatus according to the first embodiment, an Electrocardiogram (FOG) gating unit creates a gate signal synchronized with an electrocardiographic signal of a subject, and transmits the created gate signal to a real-time sequencer. The real-time sequencer then transmits sequence information (information for specifying strength, timing, and the like) to a gradient magnetic-field power source, a transmitting unit for a Radio Frequency wave (RF) pulse, and the like, so as to be synchronized with the received gate signal. The gradient magnetic-field power source, the transmitting unit, and the like execute a sequence in accordance with the received sequence information, so that the subject is imaged.

In the MRI apparatus according to the first embodiment, a raw-data buffer substrate intermediates between a receiving unit that acquires a magnetic resonance signal (hereinafter, "MRI echo signal") and a raw-data collecting unit that collects raw data, buffers raw data acquired by the receiving unit, and then transfers the raw data to the raw-data collecting unit.

In the MRI apparatus according to the first embodiment, the ECG gating unit detects an irregular synchronization interval with respect to an electrocardiographic signal (hereinafter, referred to as "BAD beat" as required), and notifies the real-time sequencer that a BAD beat is detected.

On the other hand, when receiving a notice of detection of a BAD beat, the real-time sequencer notifies so the raw-data buffer substrate. The raw-data buffer substrate then provides control such that buffered raw data is not to be transferred.

Moreover, the real-time sequencer transmits sequence information to the gradient magnetic-field power source, the transmitting unit, and the like, so as to reacquire raw data equivalent to the data that is controlled not to be transferred. For example, by re-transmitting sequence information as was used about one Repetition Time (TR) earlier, the real-time sequencer provides control so as to reacquire raw data equivalent to the data that is controlled not to be transferred.

The gradient magnetic-field power source, the transmitting unit, and the like then execute a sequence in accordance with the received sequence information, i.e., the sequence information as was used about one TA earlier, so that the subject is imaged again.

In this way, the MRI apparatus according to the first embodiment provides control such that acquired raw data is once buffered in the raw-data buffer substrate, and then transferred to the raw-data collecting unit in the subsequent stage only when an electrocardiographic signal indicates a regular synchronization interval; by contrast, when an electrocardiographic signal indicates an irregular synchronization interval, acquired raw data is not transferred, and is reacquired. For this reason, even if irregularity in the heart beat is induced by a motion or an irregular pulse of the subject, recovery of raw data is automatically carried out, so that imaging does not need to be performed from the beginning. As a result, a time required for imaging is reduced, and a binding hour onto the subject the time required for the subject to be bound to the imaging apparatus is also reduced.

Figure 2:
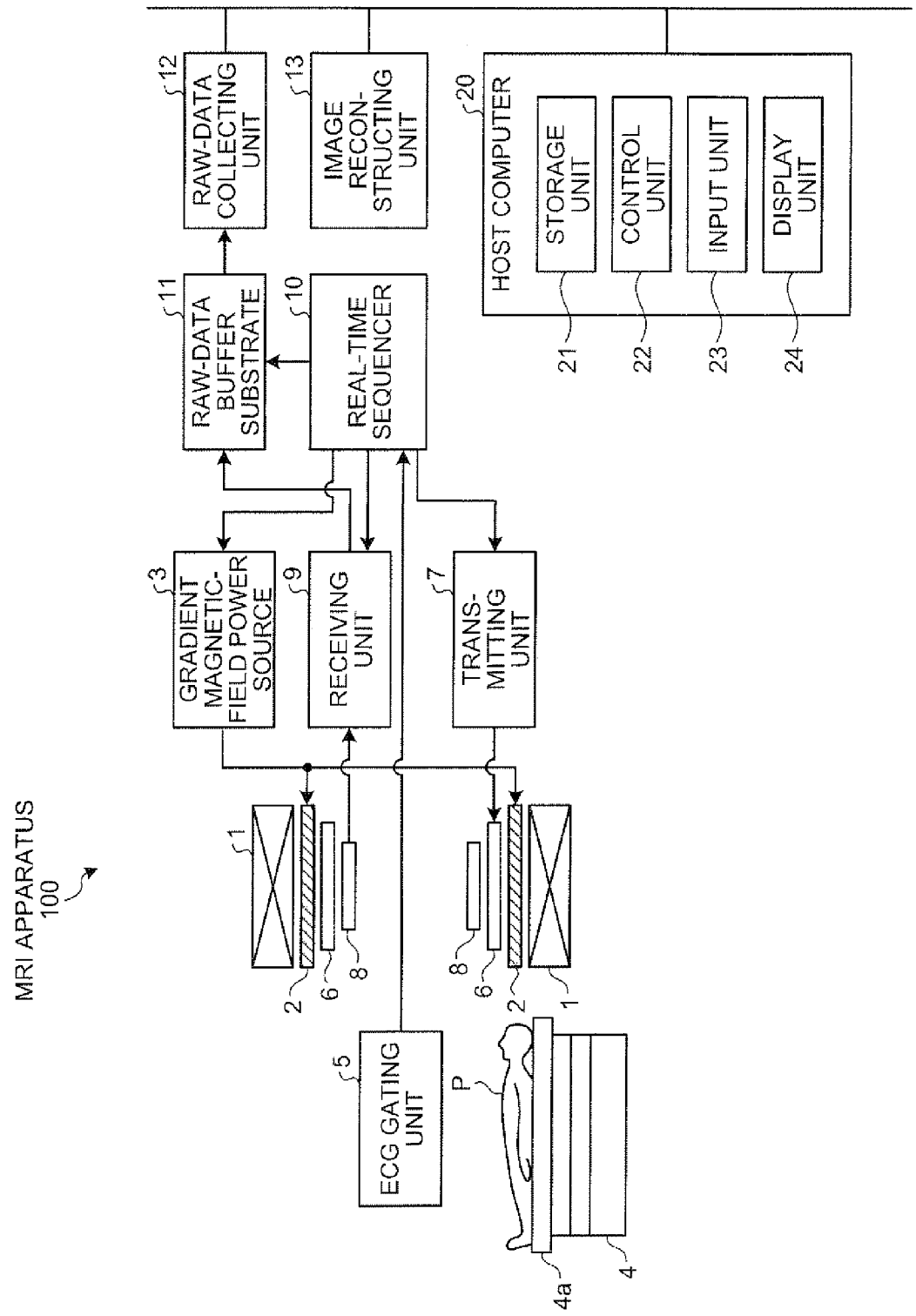
FIG. 2 is a functional block diagram of a configuration of the MRI apparatus according to the first embodiment.

Then, a configuration of the MAI apparatus according to the first embodiment is explained below with reference to FIGS. 2 to 6. FIG. 2 is a functional block diagram of a configuration of the MRI apparatus according to the first embodiment.

As shown in FIG. 2, an MRI apparatus 100 mainly includes a static magnetic-field magnet 1, a gradient magnetic-field coil 2, a gradient magnetic-field power source 3, a couch 4, an ECG gating unit 5, an RF transmitting coil 6, a transmitting unit 7, an RF receiving coil 8, a receiving unit 9, a real-time sequencer 10, a raw-data buffer substrate 11, a raw-data collecting unit 12 (which serves as data collection memory), an image reconstructing unit 13, and a host computer 20.

The static magnetic-field magnet 1 is formed in a hollow drum shape, and generates a uniform static magnetic field in its inside space. For example, a permanent magnet, or a super conducting magnet is used as the static magnetic-field magnet 1.

The gradient magnetic-field coil 2 is formed in a hollow drum shape, and generates a gradient magnetic field in its inside space. Specifically, the gradient magnetic-field coil 2 is arranged inside the static magnetic-field magnet 1, and generates a gradient magnetic field by receiving supply of a current from the gradient magnetic-field power source 3. The gradient magnetic-field coil 2 is formed of three coils in combination corresponding to x, y, and z axes orthogonal to one another, and the three coils generate gradient magnetic fields of which field strengths vary along three directions of the x, y, and z axes, respectively, by individually receiving supply of a current from the gradient magnetic-field power source 3. It is assumed that the z axis direction is the same direction as that of the static magnetic field.

The respective gradient magnetic fields of the x, y, and z axes generated by the gradient magnetic-field coil 2 correspond to, for example, a slice-selective gradient magnetic field Gs, a phase encoding gradient magnetic field Ge, and a readout gradient magnetic field Gr, respectively. The slice-selective gradient magnetic field Gs is used for arbitrarily setting a scan cross section. The phase encoding gradient magnetic field Ge is used for changing the phase of a magnetic resonance signal in accordance with a spatial position. The readout gradient magnetic field Gr is used for changing the frequency of a magnetic resonance signal in accordance with a spatial position.

The gradient magnetic-field power source 3 supplies a current to the gradient magnetic-field coil 2. Specifically, under the control of the real-time sequencer 10, the gradient magnetic-field power source 3 executes a sequence in accordance with sequence information received from the real-time sequencer 10, and supplies a current to the gradient magnetic-field coil 2. Sequence information will be described later.

The couch 4 includes a top plate 4a on which a subject P is to be placed, and inserts the top plate 4a on which the subject P is placed into a hole (a scanning space) of the gradient magnetic-field coil 2. Usually, the couch 4 is placed such that the longitudinal direction of the couch 4 is to be parallel to the central axis of the static magnetic-field magnet 1.

The ECG gating unit 5 creates a gate signal synchronized with an electrocardiographic signal of the subject F. Specifically, the ECG gating unit 5 includes an ECG sensor, and an ECG unit. The ECG sensor is attached onto a body surface of the subject P, detects ECG signals of the subject P, such as a heart beat, a pulse wave, and a breath, as an electric signal. Moreover, the ECG unit performs various processing including A/D conversion processing and delay processing on an ECG signal detected by the ECG sensor, then creates a gate signal, and transmits the created gate signal to the real-time sequencer 10.

A timing chart of ECG gating is explained below with reference to FIG. 3. FIG. 3 is an ECG-gating timing chart. To begin with, the ECG gating unit 5 detects an ECG signal shown in FIG. 3 as an electric signal, then performs A/D conversion processing on the detected ECG signal, and creates a QRS synchronized signal shown in FIG. 3. Then, the ECG gating unit 5 performs delay processing on the created QRS synchronized signal, and then creates a gate signal shown in FIG. 3. The ECG gating unit 5 then transmits the created gate signal to the real-time sequencer 10. After that, as shown in FIG. 3, under the control of the real-time sequencer 10, a sequence is executed by the gradient magnetic-field power source 3, the transmitting unit 7, and the receiving unit 9, and the receiving unit 9 acquires an MRI echo signal, performs A/D conversion processing, and acquires raw data.

Moreover, the ECG gating unit 5 detects a BAD beat with respect to electrocardiographic signals of the subject P, and notifies the real-time sequencer 10 that a BAD beat is detected.

A method of BAD beat detection performed by the ECG gating unit 5 is explained below with reference to an example. However, methods of BAD beat detection are not limited to the method explained below. The ECG unit according to the first embodiment preliminarily determines criteria for evaluation of a regular synchronization interval based on an average interval of intervals of appearances of a characteristic wave (for example, an average interval of R-wave intervals) in an electrocardiogram waveform of the subject P detected by the ECG sensor.

For example, the ECG unit according to the first embodiment calculates an average time of R-wave intervals in an electrocardiogram waveform preliminarily detected by the ECG sensor prior to the start of imaging, and assumes that the calculated average time of R-wave intervals is the regular synchronization interval. For example, the ECG unit calculates the average time of R-wave intervals to "one second", and assumes that "one second" is the regular synchronization interval. The ECG unit then calculates an acceptable time range as normal heart beat that is an acceptable range of one heart beat, from the average time of R-wave intervals assumed as the regular synchronization interval. For example, when "one second" is the regular synchronization internal, the ECG unit calculates an acceptable time range as normal heart beat to between 0.9 second and 1.1 second, based on a preset setting value (for example, 10%).

The ECG unit according to the first embodiment then detects an R-wave interval in an electrocardiogram waveform detected by the ECG sensor after the imaging is started; and if the detected R-wave interval falls within the acceptable time range as normal heart beat, the ECG unit determines that the detected R-wave interval is the regular synchronization interval. By contrast, if the detected R-wave interval does not fall within the acceptable time range as normal heart beat, the ECG unit determines that the detected R-wave interval is an irregular synchronization interval. For example, when a detected R-wave interval is "0.95 second", the ECG unit determines that it is the regular synchronization interval; and when a detected R-wave interval is "0.5 second", the ECG unit determines that it is an irregular synchronization interval.

For example, suppose irregularity in the heart beat is induced by a motion or an irregular pulse of the subject 2, and an irregular synchronization interval appears in an R-wave interval, as shown in FIG. 4. When the irregular synchronization interval appears, the ECG unit according to the first embodiment detects the R-wave interval in timing after a sequence is executed during the irregular synchronization interval, as shown in FIG. 4. FIG. 4 is an ECG-gating timing chart.

The RF transmitting coil 6 generates a radio-frequency magnetic field. Specifically, the RF transmitting coil 6 is arranged inside the gradient magnetic-field coil 2, and generates a radio-frequency magnetic field by receiving supply of an RF pulse from the transmitting unit 7.

The transmitting unit 7 transmits an RF pulse corresponding to a Larmor frequency to the RF transmitting coil 6. Specifically, under the control of the real-time sequencer 10, the transmitting unit 7 executes a sequence in accordance with sequence information received from the real-time sequencer 10, and transmits an RF pulse to the RF transmitting coil 6. Sequence information will be described later.

The RF receiving coil 8 receives an MRI echo signal. Specifically, the RF receiving coil 8 is arranged inside the gradient magnetic-field coil 2, and receives an MRI echo signal emitted from the subject P owing to an influence of the radio-frequency magnetic field. Moreover, the RE receiving coil 8 transmits the received MRI echo signal to the receiving unit 9.

The receiving unit 9 creates raw data of an MRI echo signal. Specifically, under the control of the real-time sequencer 10, the receiving unit 9 executes a sequence in accordance with sequence information received from the real-time sequencer 10, and receives an MRI echo signal from the RF receiving coil 8. Moreover, the receiving unit 9 creates raw data of the received MRI echo signal, and then transmits the created raw data to the raw-data buffer substrate 11. For example, the receiving unit 9 performs various signal processing on an MRI echo signal, for example, pre-amplification, intermediate frequency transformation, phase detection, low frequency amplification, and filtering, then performs analog-to-digital (A/D) conversion, and creates raw data.

The real-time sequencer 10 stores therein sequence information transmitted from the host computer 20, and controls the gradient magnetic-field power source 3, the transmitting unit 7, and the receiving unit 9 in accordance with the stored sequence information. Specifically, the real-time sequencer 10 transmits sequence information to the gradient magnetic-field power source 3, the transmitting unit 7, and the receiving unit 9, so as to be synchronized with a gate signal received from the BOG gating unit 5. Moreover, when receiving a notice of detection of a BAD beat from the ECG gating unit 5, the real-time sequencer 10 notifies the raw-data buffer substrate 11. Furthermore, when receiving a notice of detection of a BAD beat from the BOG gating unit 5, the real-time sequencer 10 transmits sequence information to the gradient magnetic-field power source 3, the transmitting unit 7, and the receiving unit 9 so as to reacquire raw data equivalent to data of which acquisition ends in failure. For example, the real-time sequencer 10 provides control so as to reacquire raw data equivalent to data that is controlled not to be transferred, by transmitting sequence information as was used about one TR earlier.

Sequence information is explained below with reference to an example. However, sequence information and imaging methods are not limited to the following description explained below. Sequence information is for operating the gradient magnetic-field power source 3, the transmitting unit 7, and the receiving unit 9 in accordance with a series of sequences. It is assumed that the MRI apparatus 100 according to the first embodiment is configured to use, for example, a fast spin echo method as an imaging method, as shown in FIG. 5. In other words, the MRI apparatus 100 is configured to acquire one MRI echo signal with respect to one heart beat, and acquired MRI echo signals are sequentially arranged from the center part of a k-space toward its edges as shown in FIG. 5, for example, from a first MRI echo (echo 1) signal to a ninth MRI echo signal (echo 9). FIG. 5 is a schematic diagram for explaining the imaging method.

Under such imaging method, the real-time sequencer 10 according to the first embodiment stores therein sequence information as shown in FIG. 6. For example, the real-time sequencer 10 stores the strengths and the supply timings of respective currents to be supplied to three coils corresponding to respective axes of x, y, and z, as sequence information for controlling the gradient magnetic-field power source 3. For convenience of explanation, strengths and supply timings of currents to be supplied to the three coils are not distinguished in FIG. 6. Moreover, for example, the real-time sequencer 10 stores the strength and the transmitting timing of an RF pulse as sequence information for controlling the transmitting unit 7. Furthermore, for example, the real-time sequencer 10 stores the receiving timing of an MRI echo signal as sequence information for controlling the receiving unit 9. FIG. 6 is a schematic diagram for explaining sequence information.

In other words, the real-time sequencer 10 according to the first embodiment transmits to the gradient magnetic-field power source 3, the transmitting unit 7, and the receiving unit 9, sequence information stored by being each associated with a TR number of a sequence to be executed at present, so as to execute in order a series of sequences indicated as TR 1 to TR 9. For example, the real-time sequencer 10 includes a pointer as shown in FIG. 6, and manages the TR number of a sequence to be executed at present, by moving the pointer by one TR when executing the series of the sequences.

The raw-data buffer substrate 11 buffers raw data acquired by the receiving unit 9, and then transfers the raw data to the raw-data collecting unit 12. Specifically, the raw-data buffer substrate 11 intermediates between the receiving unit 9 and the raw-data collecting unit 12, and includes regions of a double buffer structure (volatile memories) configured to buffer therein raw data of two heart-beat equivalent (i.e., raw data acquired between two heart beats), and a logic gate unit, such as a Field Programmable Gate Array (FPGA).

The volatile memories alternately buffer raw data acquired by the receiving unit 9 by one heart beat. The logic gate unit controls transferring and not-transferring of raw data buffered in the volatile memories. For example, the logic gate unit according to the first embodiment provides control such that when a certain time has elapsed since buffering of raw data buffered in the volatile memory (for example, when a time period has elapsed during which it is supposed to receive detection of a BAD beat if it is detected), the raw data buffered in the volatile memory is transferred to the raw-data collecting unit 12 in the subsequent stage. On the other hand, when receiving a notice detection of a BAD beat from the real-time sequencer 10, the logic gate unit provides control such that raw data buffered in the volatile memory is not to be transferred to the raw-data collecting unit 12 in the subsequent stage. The raw data that is controlled not to be transferred is to be rewritten over with raw data that will be buffered later in the volatile memory.

In this way, the raw-data buffer substrate 11 provides control such that only when an electrocardiographic signal of the subject P indicates a regular synchronization interval, raw data acquired during the regular synchronization interval is transferred to the raw-data collecting unit in the subsequent stage; and when an electrocardiographic signal indicates an irregular synchronization interval, raw data acquired during the irregular synchronization interval is not to be transferred. The reason why the raw-data buffer substrate 11 includes the regions of a double buffer structure configured to buffer raw data of at least two heart-beat equivalent is because, according to the first embodiment, determination whether a synchronization interval is regular is detected in timing after a sequence during the synchronization interval is executed. In other words, while determining whether a synchronization interval is regular, a sequence of the next TR is executed, so that raw data corresponding to the sequence of the next TR is transmitted to the raw-data buffer substrate 11. For this reason, the raw-data buffer substrate 11 according to the first embodiment includes the regions of a double buffer structure configured to buffer raw data of at least two heart-beat equivalent, and ensures a region that stores therein next raw data while determining whether the synchronization interval is regular.

The raw-data collecting unit 12 collects raw data. Specifically, the raw-data collecting unit 12 collects raw data transferred from the raw-data buffer substrate 11, performs correction processing, such as averaging processing, phase correction, and sorting, on the collected data, and stores therein the processed data. The raw data stored by the raw-data collecting unit 12 is used for reconstruction processing performed by the image reconstructing unit 13.

The image reconstructing unit 13 creates medical image data of the subject P from raw data. Specifically, the image reconstructing unit 13 performs reconstruction processing, such as a Fourier transform, on raw data stored by the raw-data collecting unit 12, and creates medical image data of the subject P.

The host computer 20 includes a storage unit 21, a control unit 22, an input unit 23, and a display unit 24, as shown in FIG. 2.

The storage unit 21 stores therein data required for overall control of the MRI apparatus 100.

The control unit 22 controls the MRI apparatus 100 overall. Specifically, the control unit 22 provides control of imaging processing performed by the real-time sequencer 10, and control of reconstruction processing performed by the image reconstructing unit 13, based on an instruction from an operator input via the input unit 23. For example, when imaging conditions are instructed by the operator, the control unit 22 creates sequence information based on the instructed imaging conditions, and transmits the created sequence information to the real-time sequencer 10.

The input unit 23 receives, for example, an instruction from the operator. For example, as the input unit 23, a pointing device, such as a mouse or a trackball, a selecting device, such as a mode switch, and an input device, such as a keyboard, can be used.

The display unit 24 displays various information, medical image data, and the like. A display device, for example, a liquid crystal display, can be used as the display unit 24.

Figure 7:
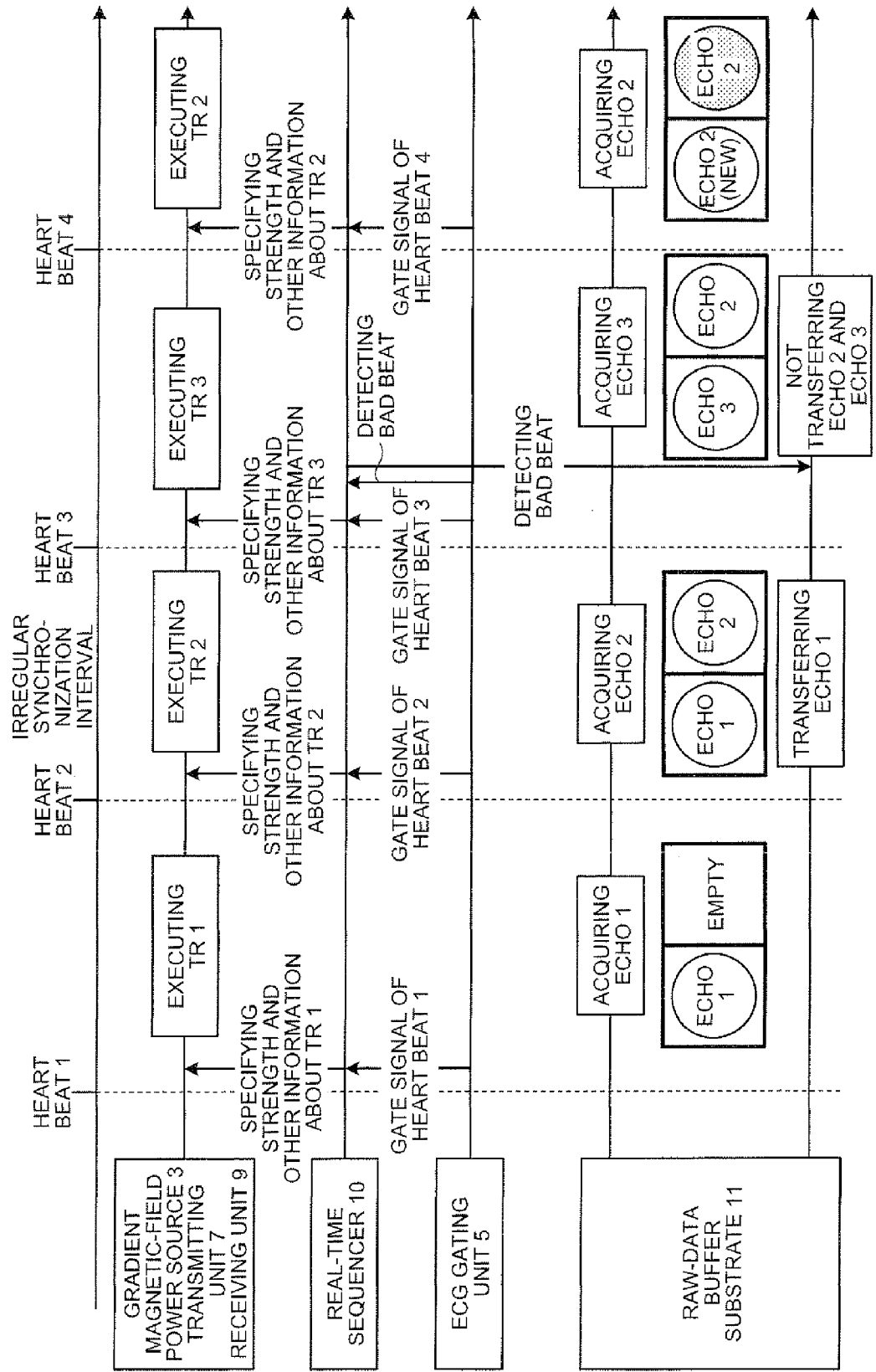
FIG. 7 is a schematic diagram for explaining transfer control on transferring raw data.

A process procedure performed by the MRI apparatus according to the first embodiment is explained below with reference to FIGS. 7 to 9. FIG. 7 is a schematic diagram for explaining transfer control on transferring raw data.

At first, with reference to FIG. 7, transfer control on transferring raw data between the ECG gating unit 5, the real-time sequencer 10, the gradient magnetic-field power source 3, the transmitting unit 7, and the raw-data buffer substrate 11 will be explained below. FIG. 7 depicts transfer control with respect to electrocardiographic signals of four heart-beat equivalent, and depicts a case where an interval between a heart beat 2 and a heart beat 3 is an irregular synchronization interval.

As shown in FIG. 7, the ECG gating unit 5 creates a gate signal from a heart beat of the subject P, and transmits the created gate signal to the real-time sequencer 10. As shown in FIG. 7, regardless of a regular synchronization interval or an irregular synchronization interval, the ECG gating unit 5 creates a gate signal with respect to every heart beat among heart beats 1 to 4, and transmits the created gate signal to the real-time sequencer 10.

Moreover, as shown in FIG. 7, when receiving a gate signal from the ECG gating unit 5, the real-time sequencer 10 transmits sequence information to the gradient magnetic-field power source 3, the transmitting unit 7, and the receiving unit 9 so as to be synchronized with the received gate signal. For example, the real-time sequencer 10 manages such that the TR number of a sequence to be executed at present during the heart beat 1 is TR 1, and transmits sequence information in order from TR 1.

As shown in FIG. 7, the gradient magnetic-field power source 3, the transmitting unit 7, and the receiving unit 9 then execute sequences in order from TR 1, under the control of the real-time sequencer 10.

On the other hand, when a sequence is executed, as shown in FIG. 7, the raw-data buffer substrate 11 buffers raw data. For example, when the sequence of TR 1 is executed, the raw-data buffer substrate 11 acquires raw data (echo 1), and stores the acquired raw data (echo 1) into one region of the double buffer structure. Moreover, the raw-data buffer substrate 11 provides control such that when a certain time has elapsed since buffering, buffered raw data is transferred to the raw-data collecting unit 12 in the subsequent stage. For this reason, in a period between the heart beat 2 and the heart beat 3, because a certain time has been elapsed since buffering of the buffered raw data (echo 1), the raw-data buffer substrate 11 transfers the buffered raw data (echo 1) to the raw-data collecting unit 12 in the subsequent stage.

In this case, the interval between the heart beat 2 and the heart beat 3 is an irregular synchronization interval. However, as shown in FIG. 7, after TR 2 is executed, it is detected that the interval between the heart beat 2 and the heart beat 3 is an irregular synchronization interval. Precisely, after the ECG gating unit 5 detects a BAD beat, the gating unit 3 notifies the real-time sequencer 10 that a BAD beat is detected in timing between the heart beat 3 and the heart beat 4, as shown in FIG. 7.

For this reason, despite the irregular synchronization interval between the heart beat 2 and the heart beat 3, the sequence of TR 2 is executed, and then, as shown in FIG. 7, the raw-data buffer substrate 11 acquires raw data (echo 2), and stores the acquired raw data (echo 2) into the other region of the double buffer structure.

On the other hand, in a period between the heart beat 3 and the heart beat 4, the ECG gating unit 5 detects that the interval between the heart beat 2 and the heart beat 3 is an irregular synchronization interval, and notifies the real-time sequencer 10 that a BAD beat is detected. The real-time sequencer 10 then notifies the raw-data buffer substrate 11 that a BAD beat is detected, and turns back the pointer that manages the TR number of a sequence to be executed at present to one TR earlier. Precisely, when the pointer is positioned at "TR 3" as the TR number of the sequence to be executed at present, the real-time sequencer 10 turns back the pointer by one TR, and moves it to "TR 2". If the implementation is such that immediately after execution of "TR 3", the pointer moves to "TR 4", and when a BAD beat is notified, the pointer is already positioned at "TR 4"; the pointer is to be turned back by two TRs.

On the other hand, as shown in FIG. 7, when TR 3 is executed during the interval between the heart beat 3 and the heart beat 4, the raw-data buffer substrate 11 acquires raw data (echo 3), and stores the acquired raw data (echo 3) into one region of the double buffer structure. Precisely, the raw-data buffer substrate 11 stores raw data (echo 2) and raw data (echo 3). Because the certain time has not been elapsed since buffering of the buffered raw data (echo 2), the raw-data buffer substrate 11 has not transferred the raw data (echo 2) to the raw-data collecting unit 12 in the subsequent stage. At this stage, when receiving a notice that a BAD beat is detected, the raw-data buffer substrate 11 provides control such that the buffered raw data are not to be transferred to the raw-data collecting unit 12 in the subsequent stage. The raw data (echo 2) and the raw data (echo 3) that are controlled not to be transferred are to be rewritten over with raw data that will be buffered later.

Subsequently, the ECG gating unit 5 creates a gate signal from the heart beat 4 of the subject P, and transmits the created gate signal to the real-time sequencer 10. When receiving the gate signal from the ECG gating unit 5, the real-time sequencer 10 then transmits sequence information to the gradient magnetic-field power source 3, the transmitting unit 7, and the receiving unit 9 so as to be synchronized with the received gate signal. At that moment, the pointer is positioned at "TR 2" as the TR number of a sequence to be executed at present, therefore, the real-time sequencer 10 transmits sequence information about "TR 2" to the gradient magnetic-field power source 3, the transmitting unit 7, and the receiving unit 9. The gradient magnetic-field power source 3, the transmitting unit 7, and the receiving unit 9 then execute the sequence of TR 2.

As a result, when the sequence of TR 2 is executed, the raw-data buffer substrate 11 buffers raw data (echo 2). The newly buffered raw data (echo 2) is a reacquired equivalent of the raw data (echo 2) that is controlled not to be transferred a short while ago.

Figure 8A:
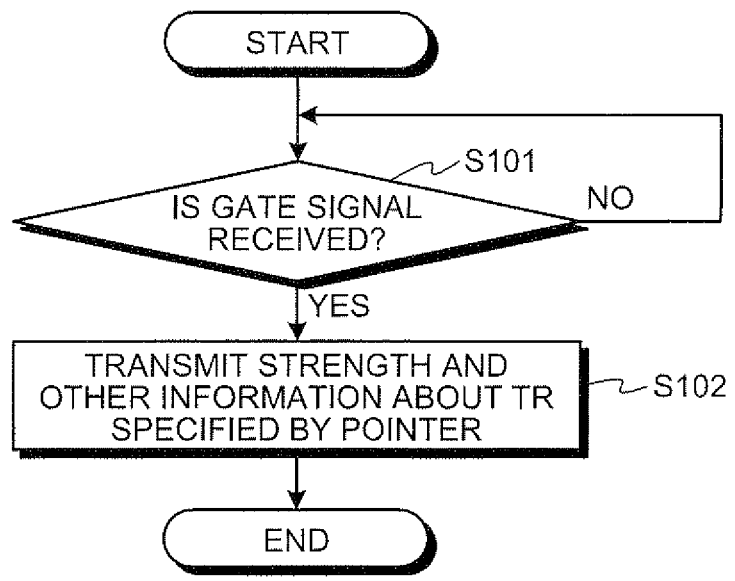
FIGS. 8A and 8B are flowcharts of process procedures performed by a real-time sequencer.
Figure 8B:
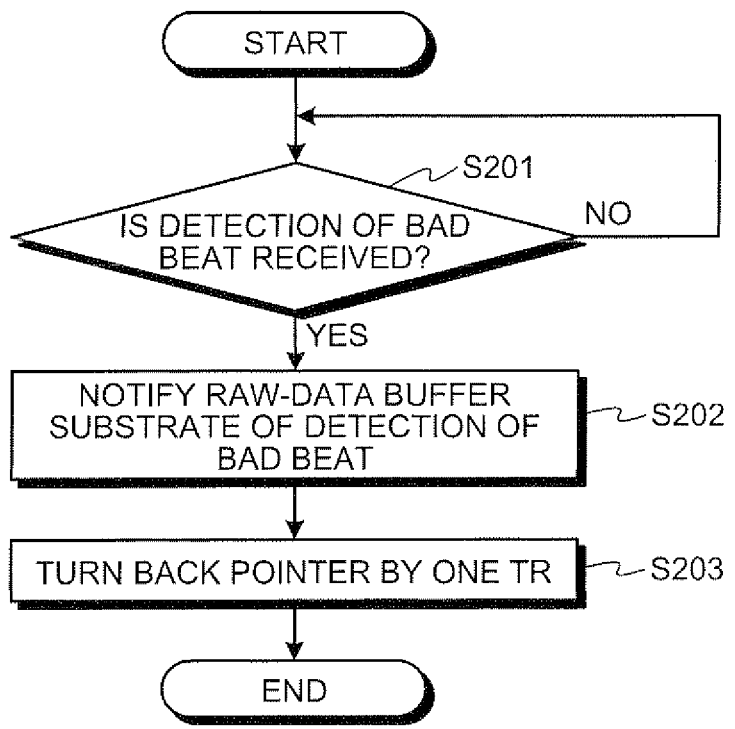

Then, a process procedure performed by the real-time sequencer is explained below with reference to FIGS. 8A and 8B. FIGS. 8A and 8B are flowcharts of process procedures performed by the real-time sequencer.

As shown in FIG. 8A, the real-time sequencer 10 according to the first embodiment determines whether a gate signal is received from the ECG gating unit 5 (Step S101); and if it is received (Yes at Step S101), the real-time sequencer 10 transmits sequence information associated with a TR number specified by the pointer as the TR number of a sequence to be executed at present to the gradient magnetic-field power source 3, the transmitting unit 7, and the receiving unit 9 (Step S102).

Moreover, as shown in FIG. 8B, the real-time sequencer 10 according to the first embodiment determines whether a notice that a BAD beat is detected is received from the ECG gating unit 5 (Step S201); and if it is received (Yes at Step S201), the real-time sequencer 10 notifies so the raw-data buffer substrate 11 (Step S202). The real-time sequencer 10 then turns back the pointer by one TR (Step S203).

A process procedure performed by the raw-data buffer substrate is explained below with reference to FIG. 9. FIG. 9 is a flowchart of a process procedure performed by the raw-data buffer substrate.

Figure 9:
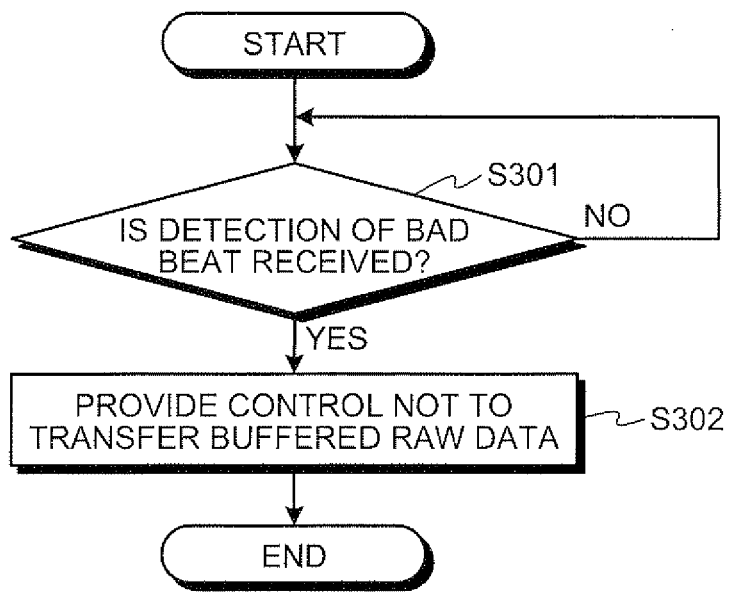
FIG. 9 is a flowchart of a process procedure performed by a raw-data buffer substrate.

As shown in FIG. 9, the raw-data buffer substrate 11 determines whether a notice that a BAD beat is detected is received from the real-time sequencer 10 (Step S301); and if it is received (Yes at Step S301), the raw-data buffer substrate 11 provides control such that buffered raw data is not to be transferred (Step S302).

As described above, in the MRI apparatus 100 according to the first embodiment, the receiving unit 9 acquires raw data about the subject P in a synchronized manner with an electrocardiographic signal of the subject P. The raw-data collecting unit 12 collects the raw data acquired by the receiving unit 9. According to the first embodiment, the raw-data buffer substrate 11 intermediates between the receiving unit 9 and the raw-data collecting unit 12, buffers the raw data acquired by the receiving unit 9, and then transfers the raw data to the raw-data collecting unit 12. On the other hand, the ECG gating unit 5 detects an irregular synchronization interval with respect to an electrocardiographic signal. When the ECG gating unit 5 detects an irregular synchronization interval, a notice of the detection is given to the raw-data buffer substrate 11 via the real-time sequencer 10, and then the raw-data buffer substrate 11 provides control such that the buffered raw data is not to be transferred to the raw-data collecting unit 12. Moreover, when the ECG gating unit 5 detects the irregular synchronization interval, the real-time sequencer 10 controls the gradient magnetic-field power source 3, the transmitting unit 7, and the receiving unit 9 so as to reacquire raw data equivalent to the data that is controlled not to be transferred.

In this way, the MRI apparatus 100 according to the first embodiment provides control such that acquired raw data is once buffered in the raw-data buffer substrate 11, and then transferred to the raw-data collecting unit 12 in the subsequent stage only when an electrocardiographic signal indicates a regular synchronization interval; by contrast, when it indicates an irregular synchronization interval, the acquired raw data is not transferred, and is reacquired. For this reason, even if irregularity in the heart beat is induced by a motion or an irregular pulse of the subject, recovery of raw data is automatically carried out, so that imaging does not need to be performed from the beginning. As a result, a time required for imaging is reduced, and a binding hour onto the subject is also reduced.

Moreover, the raw-data buffer substrate 11 according to the first embodiment includes regions configured to buffer therein raw data of at least two heart-beat equivalent.

Accordingly, a region that stores next raw data while determining whether a synchronization interval is regular can be ensured.

Furthermore, the MRI apparatus 100 according to the first embodiment can appropriately deal with the correction processing performed in an earlier stage in advance of the reconstruction processing by using a method of buffering acquired raw data once in the raw-data buffer substrate 11. In other words, as described above, the raw-data collecting unit 12 according to the first embodiment performs the correction processing, such as averaging processing, phase correction, and sorting, on raw data transferred from the raw-data buffer substrate 11.

Suppose the MRI apparatus 100 according to the first embodiment does not include the raw-data buffer substrate 11, and suppose raw data is transferred to the raw-data collecting unit 12 even when a BAD beat is detected. For example, it is assumed that when an interval between the heart beat 2 and the heart beat 3 is an irregular synchronization interval, acquired raw data (echo 2) is directly transferred to the raw-data collecting unit 12. In such case, when the raw data (echo 2) is transferred to the raw-data collecting unit 12, for example, the raw-data collecting unit 12 may immediately execute averaging processing between already acquired raw data (echo 2) and the present transferred raw data (echo 2) in some cases.

After that, even if it is notified that the transferred raw data (echo 2) is raw data acquired during the irregular synchronization interval, it is too late and difficult for the raw-data collecting unit 12 to execute processing of excluding the raw data acquired during the irregular synchronization interval from the data already processed through the averaging processing.

Compared with this, according to the MRI apparatus 100 according to the first embodiment, raw data acquired during an irregular synchronization interval is not to be transferred to the raw-data collecting unit 12. Accordingly, the raw-data collecting unit 12 does not perform the correction processing by using raw data acquired during an irregular synchronization interval. In this way, the MRI apparatus 100 according to the first embodiment can appropriately deal with the correction processing performed in an earlier stage in advance of the reconstruction processing by using a method of buffering acquired raw data once into the raw-data buffer substrate 11.

Explained above as the first embodiment is a method that the raw-data buffer substrate 11 includes regions configured to buffer therein raw data of two heart-beat equivalent, and provides control not to transfer raw data acquired during a synchronization interval of a BAD beat when the BAD beat is detected. In other words, it is a method of reacquiring raw data by turning back by one heart-beat equivalent. However, the present invention is not limited to the method.

In a second embodiment of the present invention, explained below is a method that the raw-data buffer substrate 11 includes regions configured to buffer therein raw data of a plurality of heart-beat equivalent more than at least two heart beats (for example, five heart-beat equivalent), and provides control not to transfer raw data of a preset number of heart-beat equivalent when a BAD beat is detected. In other words, it is a method of reacquiring raw data by turning back by a certain number of heart-beat equivalent.

Figure 10:
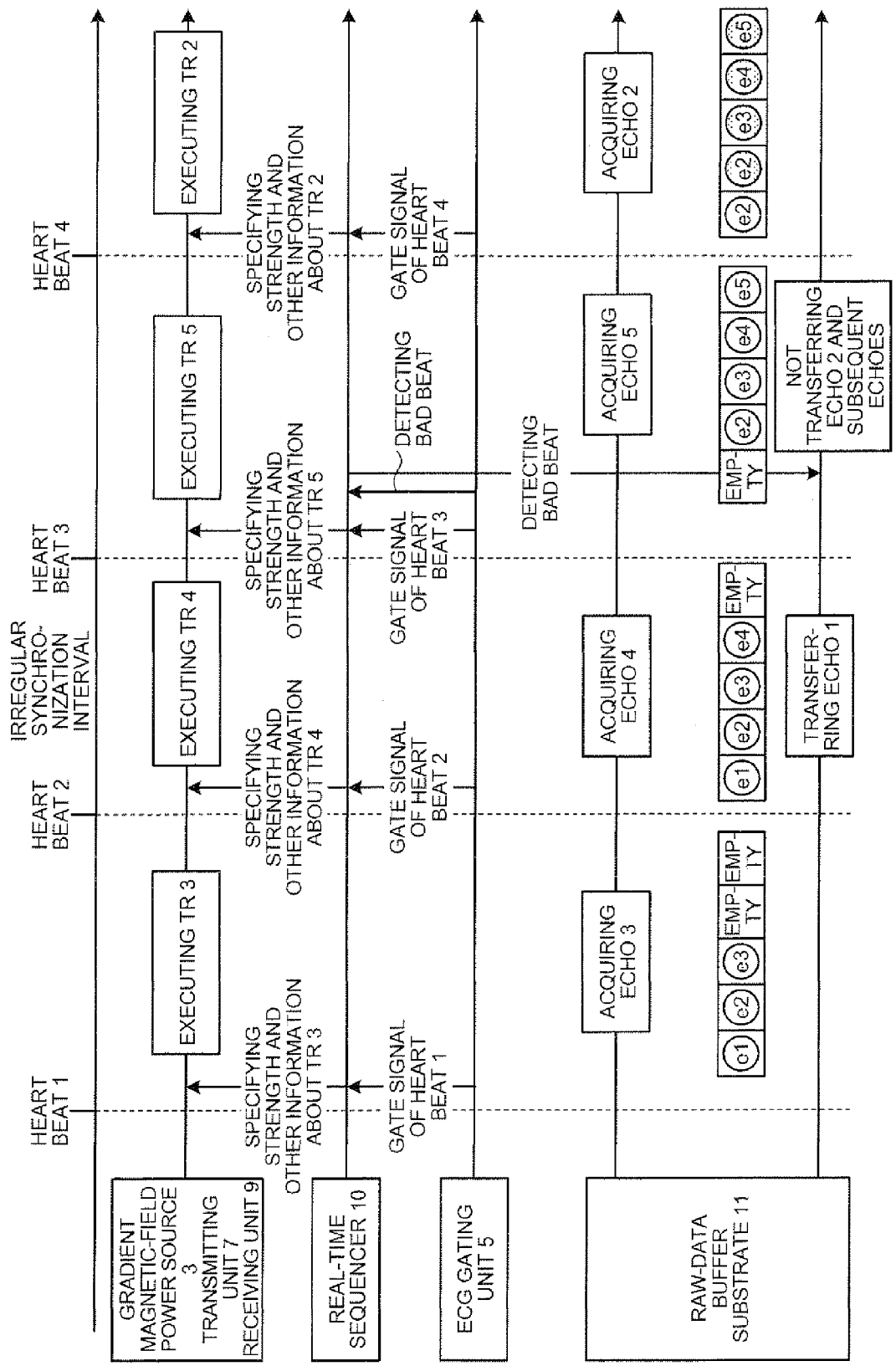
FIG. 10 is a schematic diagram for explaining transfer control on transferring raw data.

A process procedure performed by the MRI apparatus according to the second embodiment is explained below with reference to FIGS. 10 and 11. FIG. 10 is a schematic diagram for explaining transfer control on transferring raw data.

Explaining the transfer control by focusing on difference from the MRI apparatus 100 according to the first embodiment shown in FIG. 7, in the MRI apparatus 100 according to the second embodiment, the raw-data buffer substrate 11 includes regions configured to buffer therein raw data of five heart-beat equivalent.

Moreover, the raw-data buffer substrate 11 is configured not to provide control of transferring raw data unless it is in timing after buffering raw data of a preset number of heart-beat equivalent, for example, three heart-beat equivalent. Precisely, for example, as shown in FIG. 10, raw data (echo 1) buffered in the raw-data buffer substrate 11 is subjected to transfer control in timing only after buffering raw data of three heart-beat equivalent, namely, raw data (echo 1), raw data (echo 2), and raw data (echo 3).

In other words, when a BAD beat is detected, it is expected that raw data of three heart-beat earlier has not been transferred yet, so that after control is provided not to transfer the raw data of three heart-beat equivalent, raw data can be reacquired by turning back by three heart-beat equivalent.

Accordingly, for example, as shown in FIG. 10, when an interval between the heart beat 2 and the heart beat 3 is an irregular synchronization interval, and when determination that the interval between the heart beat 2 and the heart beat 3 is an irregular synchronization interval is detected in timing after the heart beat 3, raw data (echo 2) to raw data (echo 4) (or raw data (echo 5) in some cases) are stored in the raw-data buffer substrate 11. Although the raw data acquired during the irregular synchronization interval is the raw data (echo 4), the raw-data buffer substrate 11 provides control such that not only the raw data (echo 4) but also the raw data of three heart-beat earlier, i.e., the raw data (echo 2), and subsequent raw data are not to be transferred.

The real-time sequencer 10 then turns back the pointer that manages the TR number of a sequence to be executed at present, to three TRs earlier. Precisely, when the pointer is positioned at "TR 5" as the TR number of the sequence to be executed at present, the real-time sequencer 10 turns back the pointer by three TRs, and moves it to "TR 2".

A process procedure performed by the real-time sequencer is explained below with reference to FIG. 11. FIG. 11 is a flowchart of a process procedure performed by the real-time sequencer.

Figure 11:
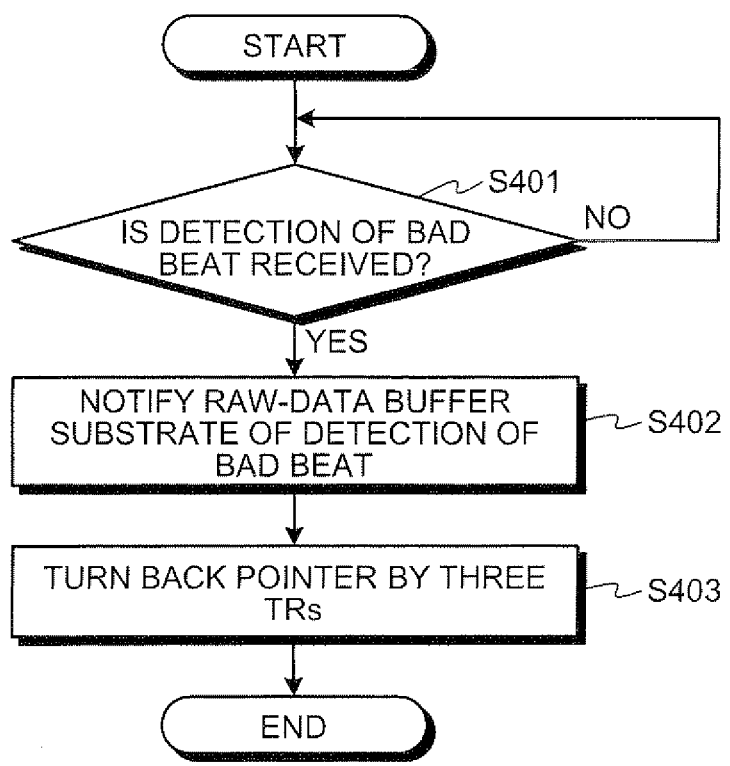
FIG. 11 is a flowchart of a process procedure performed by a real-time sequencer.

As shown in FIG. 11, the real-time sequencer 10 according to the second embodiment also determines whether a notice that a BAD beat is detected is received from the FOG gating unit 5 (Step S401); and if it is received (Yes at Step S401), the real-time sequencer 10 notifies so the raw-data buffer substrate 11 (Step S402). The real-time sequencer 10 then turns back the pointer by three TRs (Step S403).

As described above, in the MRI apparatus 100 according to the second embodiment, the raw-data buffer substrate 11 includes regions configured to buffer therein raw data of a plurality of heart-beat equivalent more than at least two heart beats. The raw-data buffer substrate 11 provides control such that after raw data of a preset number of heart-beat equivalent (for example, three heart-beat equivalent) are buffered, raw data is transferred to the raw-data collecting unit 12. When the ECG gating unit 5 detects an irregular synchronization interval, the raw-data buffer substrate 11 provides control such that the buffered raw data is not to be transferred to the raw-data collecting unit 12. Moreover, when the ECG gating unit 5 detects the irregular synchronization interval, the real-time sequencer 10 controls the gradient magnetic-field power source 3, the transmitting unit 7, and the receiving unit 9 so as to reacquire raw data equivalent to the data that is controlled not to be transferred.

In this way, when irregularity in the heart beat is induced by a motion or an irregular pulse of the subject, the MRI apparatus 100 according to the second embodiment does not automatically recover only raw data corresponding to a synchronization interval during which a BAD beat is detected, but automatically recovers raw data from slightly earlier data. For example, a BAD beat is detected based on the acceptable time range as normal heart beat. For this reason, there is a conceivable case where a heart beat is practically in a state immediately before turning to a BAD beat despite that the synchronization interval falls within the acceptable time range as normal heart beat, and such state is not a very suitable state for acquiring raw data. The MRI apparatus 100 according to the second embodiment is configured to recover raw data automatically from slightly earlier data when a BAD beat is detected, thereby being capable to collect raw data more appropriately.

The first and second embodiments are explained above with reference to an example of the imaging method of acquiring one MRI echo signal with respect to one heart beat. In such case, as explained above with reference to FIG. 5, MRI echo signals are sequentially arranged from the center part of a k-space toward its edges, from a first MRI echo signal (echo 1) to a ninth MRI echo signal (echo 9). However, the present invention is not limited to this, and can be applied to an imaging method of acquiring a plurality of MRI echo signals with respect to one heart beat.

For example, according to an imaging method of acquiring three MRI echo signals with respect to one heart beat, each three MRI echo signals per heart beat are arranged, for example, from the first MRI echo signal (echo 1) to the third MRI echo signal (echo 3), from the fourth MRI echo signal (echo 4) to the sixth MRI echo signal (echo 6), and from the seventh MRI echo signal (echo 7) to the ninth MRI echo signal (echo 9). An example where the present invention is applied to the imaging method of acquiring three MRI echo signals with respect to one heart beat is explained below as a third embodiment of the present invention.

Figure 12:
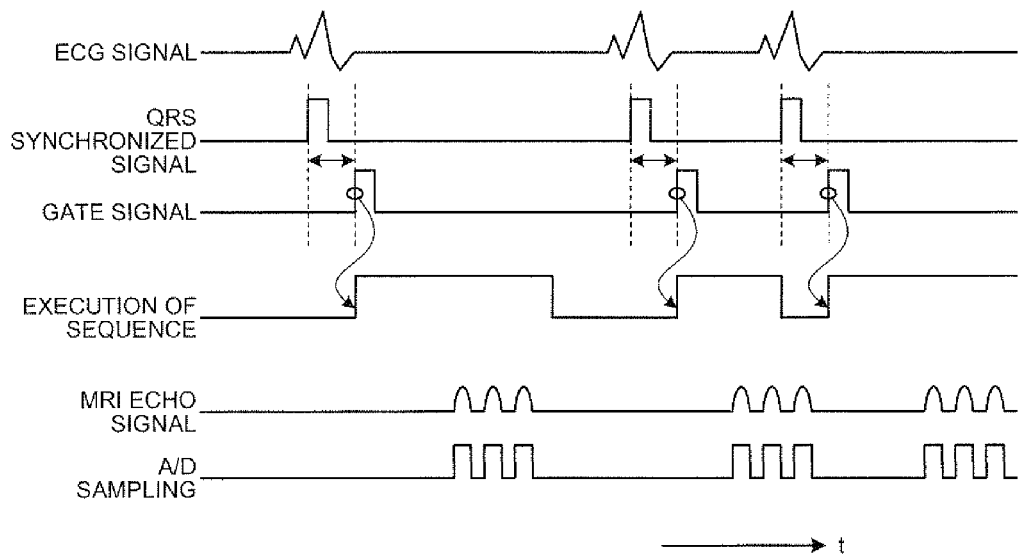
FIG. 12 is an ECG-gating timing chart.

A timing chart of ECG gating according to the third embodiment is explained below with reference to FIGS. 12 and 13. FIG. 12 is an ECG-gating timing chart. To begin with, similarly to the first and second embodiments, the ECG gating unit 5 detects an FOG signal as an electric signal, performs A/D conversion processing on the detected ECG signal, creates a QRS synchronized signal, performs delay processing on the created QRS synchronized signal, and then creates a gate signal. When the ECG gating unit 5 then transmits the created gate signal to the real-time sequencer 10 similarly to the first and second embodiments; after that, as shown in FIG. 12, under the control of the real-time sequencer 10, a sequence is executed by the gradient magnetic-field power source 3, the transmitting unit 7, and the receiving unit 9, and the receiving unit 9 acquires three MRI echo signals with respect to one heart beat, performs A/D conversion processing on each of the acquired three MRI echo signals, and acquires raw data of the three MRI echo signals.

Figure 13:
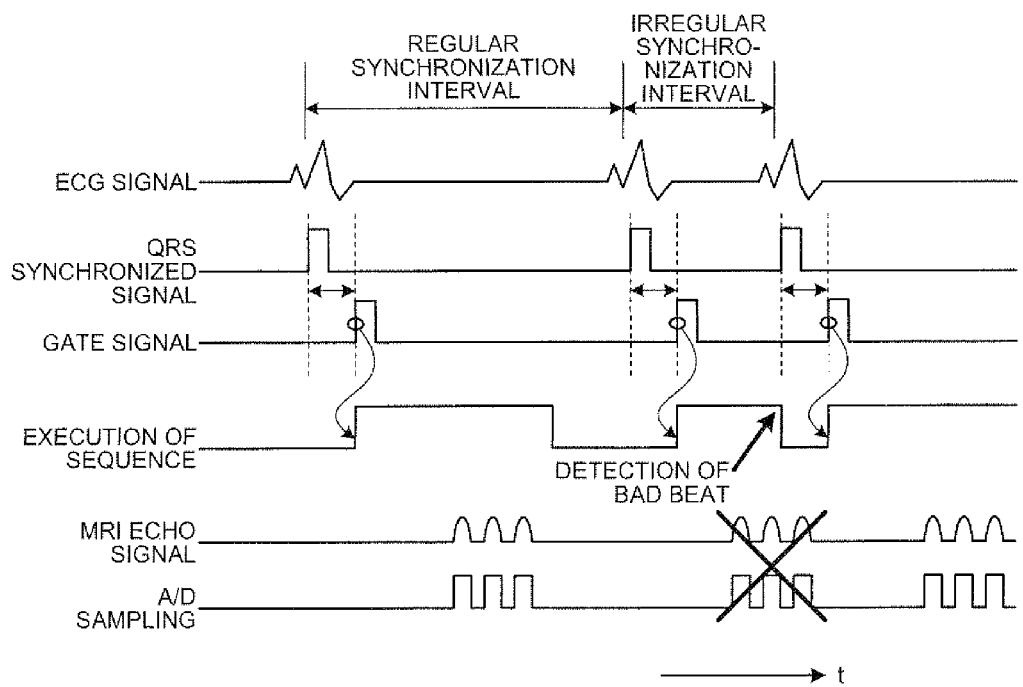
FIG. 13 is an ECG-gating timing chart.

Suppose, for example, irregularity in the heart beat is induced by a motion or an irregular pulse of the subject P, and an irregular synchronization interval appears in an R-wave interval, as shown in FIG. 13. Similarly to the first and second embodiments, as shown in FIG. 12, the ECG unit according to the third embodiment detects the R-wave interval in timing after a sequence is executed during the irregular synchronization interval, and raw data to be reacquired in this stage is generally raw data of three MRI echo-signal equivalent, as shown in FIG. 13.

Figure 14:
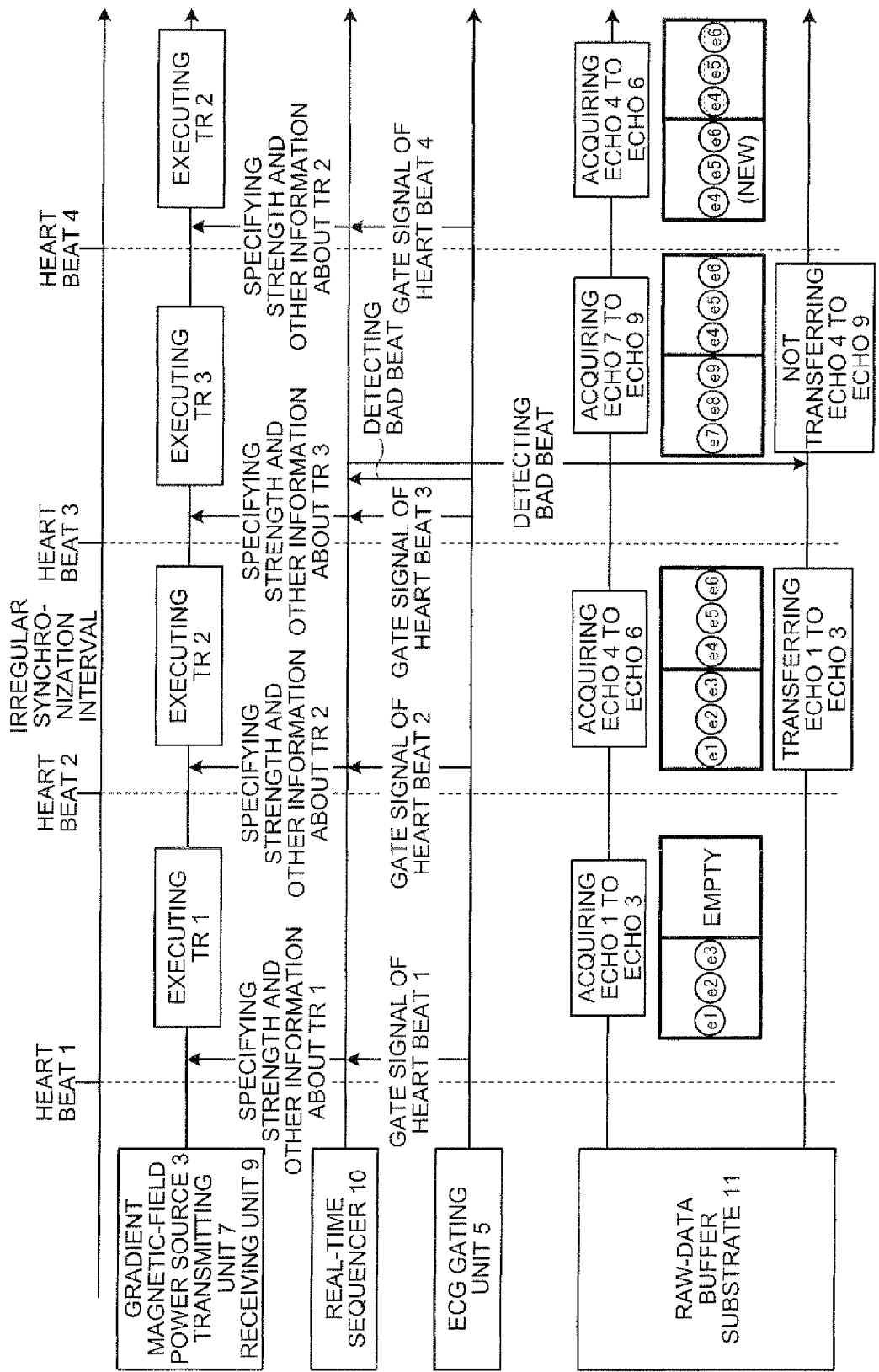
FIG. 14 is a schematic diagram for explaining transfer control on transferring raw data.

Transfer control on transferring raw data according to the third embodiment is explained below with reference to FIG. 14. FIG. 14 is a schematic diagram for explaining transfer control on transferring raw data. Similarly to the first and second embodiments, FIG. 14 depicts transfer control with respect to electrocardiographic signals equivalent to four heart beats, and depicts a case where an interval between the heart beat 2 and the heart beat 3 is an irregular synchronization interval.

As shown in FIG. 14, similarly to the first and second embodiments, the gradient magnetic-field power source 3, the transmitting unit 7, and the receiving unit 9 execute sequences in order from TR 1, under the control of the real-time sequencer 10.

On the other hand, when a sequence is executed, as shown in FIG. 14, the raw-data buffer substrate 11 buffers raw data. For example, when the sequence of TR 1 is executed, the raw-data buffer substrate 11 acquires raw data (echo 1), raw data (echo 2), and raw data (echo 3), and stores the acquired raw data (echo 1), raw data (echo 2), and raw data (echo 3), into one region of the double buffer structure.

Moreover, the raw-data buffer substrate 11 provides control such that when a certain time has elapsed since buffering, buffered raw data is transferred to the raw-data collecting unit 12 in the subsequent stage. For this reason, in a period between the heart beat 2 and the heart beat 3, because a certain time has been elapsed since buffering of the buffered raw data (echo 1), raw data (echo 2), and raw data (echo 3), the raw-data buffer substrate 11 transfers the buffered raw data (echo 1), raw data (echo 2), and raw data (echo 3) to the raw-data collecting unit 12 in the subsequent stage.

In this case, the interval between the heart beat 2 and the heart beat 3 is an irregular synchronization interval. However, as shown in FIG. 14, after TR 2 is executed, it is detected that the interval between the heart beat 2 and the heart beat 3 is an irregular synchronization interval. Precisely, after the ECG gating unit 5 detects a BAD beat, the ECG gating unit 5 notifies the real-time sequencer 10 that a BAD beat is detected in timing between the heart beat 3 and the heart beat 4, as shown in FIG. 14.

For this reason, despite the irregular synchronization interval between the heart beat 2 and the heart beat 3, the sequence of TR 2 is executed, and then, as shown in FIG. 14, the raw-data buffer substrate 11 acquires raw data (echo 4), raw data (echo 5), and raw data (echo 6), and stores the acquired raw data (echo 4), raw data (echo 5), and raw data (echo 6) into the other region of the double buffer structure.

On the other hand, in a period between the heart beat 3 and the heart beat 4, the BOG gating unit 5 detects that the interval between the heart beat 2 and the heart beat 3 is an irregular synchronization interval, and notifies the real-time sequencer 10 that a BAD beat is detected. The real-time sequencer 10 then notifies the raw-data buffer substrate 11 that a BAD beat is detected, and turns back the pointer that manages the TR number of a sequence to be executed at present to one TR earlier. Precisely, when the pointer is positioned at "TR 3" as the TR number of the sequence to be executed at present, the real-time sequencer 10 turns back the pointer by one TR, and moves it to "TR 2". If the implementation is such that immediately after execution of "TR 3", the pointer moves to "TR 4", and when a BAD beat is notified, the pointer is already positioned at "TR 4"; the pointer is to be turned back by two TRs.

On the other hand, as shown in FIG. 14, when the sequence of TR 3 is executed during the interval between the heart beat 3 and the heart beat 4, the raw-data buffer substrate 11 acquires raw data (echo 7), raw data (echo 8), and raw data (echo 9), and stores the acquired raw data (echo 7), raw data (echo 8), and raw data (echo 9) into one region of the double buffer structure.

Precisely, the raw-data buffer substrate 11 stores the raw data (echo 4), raw data (echo 5), and raw data (echo 6), and the raw data (echo 7), raw data (echo 8), and raw data (echo 9). Because the certain time has not been elapsed since buffering of the buffered raw data (echo 4), raw data (echo 5), and raw data (echo 6), the raw-data buffer substrate 11 has not transferred the raw data (echo 4), raw data (echo 5), and raw data (echo 6) to the raw-data collecting unit 12 in the subsequent stage.

At this stage, when receiving a notice that a BAD beat is detected, the raw-data buffer substrate 11 provides control such that the buffered raw data are not to be transferred to the raw-data collecting unit 12 in the subsequent stage. The raw data (echo 4), raw data (echo 5), and raw data (echo 6), and the raw data (echo 7), raw data (echo 8), and raw data (echo 9) that are controlled not to be transferred are to be rewritten over with raw data that will be buffered later.

Subsequently, the ECG gating unit 5 creates a gate signal from the heart beat 4 of the subject P, and transmits the created gate signal to the real-time sequencer 10. When receiving the gate signal from the ECG gating unit 5, the real-time sequencer 10 then transmits sequence information the gradient magnetic-field power source 3, the transmitting unit 7, and the receiving unit 9 so as to be synchronized with the received gate signal. At that moment, the pointer is positioned at "TR 2" as the TR number of a sequence to be executed at present, so that the real-time sequencer 10 transmits sequence information about "TR 2" to the gradient magnetic-field power source 3, the transmitting unit 7, and the receiving unit 9. The gradient magnetic-field power source 3, the transmitting unit 7, and the receiving unit 9 then execute the sequence of TR 2.

As a result, when the sequence of TR 2 is executed, the raw-data buffer substrate 11 buffers raw data (echo 4), raw data (echo 5), and raw data (echo 6). The newly buffered raw data (echo 4), (echo 5), and (echo 6) are reacquired equivalents of the raw data (echo 4), (echo 5), and (echo 6) that are controlled not to be transferred a short while ago.

According to the first to third embodiments, although it is assumed that the MRI apparatus 100 includes the raw-data buffer substrate 11, the present invention is not limited to this, and the MRI apparatus 100 does not necessarily include the raw-data buffer substrate 11. The MRI apparatus 100 according to a fourth embodiment of the present invention is explained below.

Figure 15:
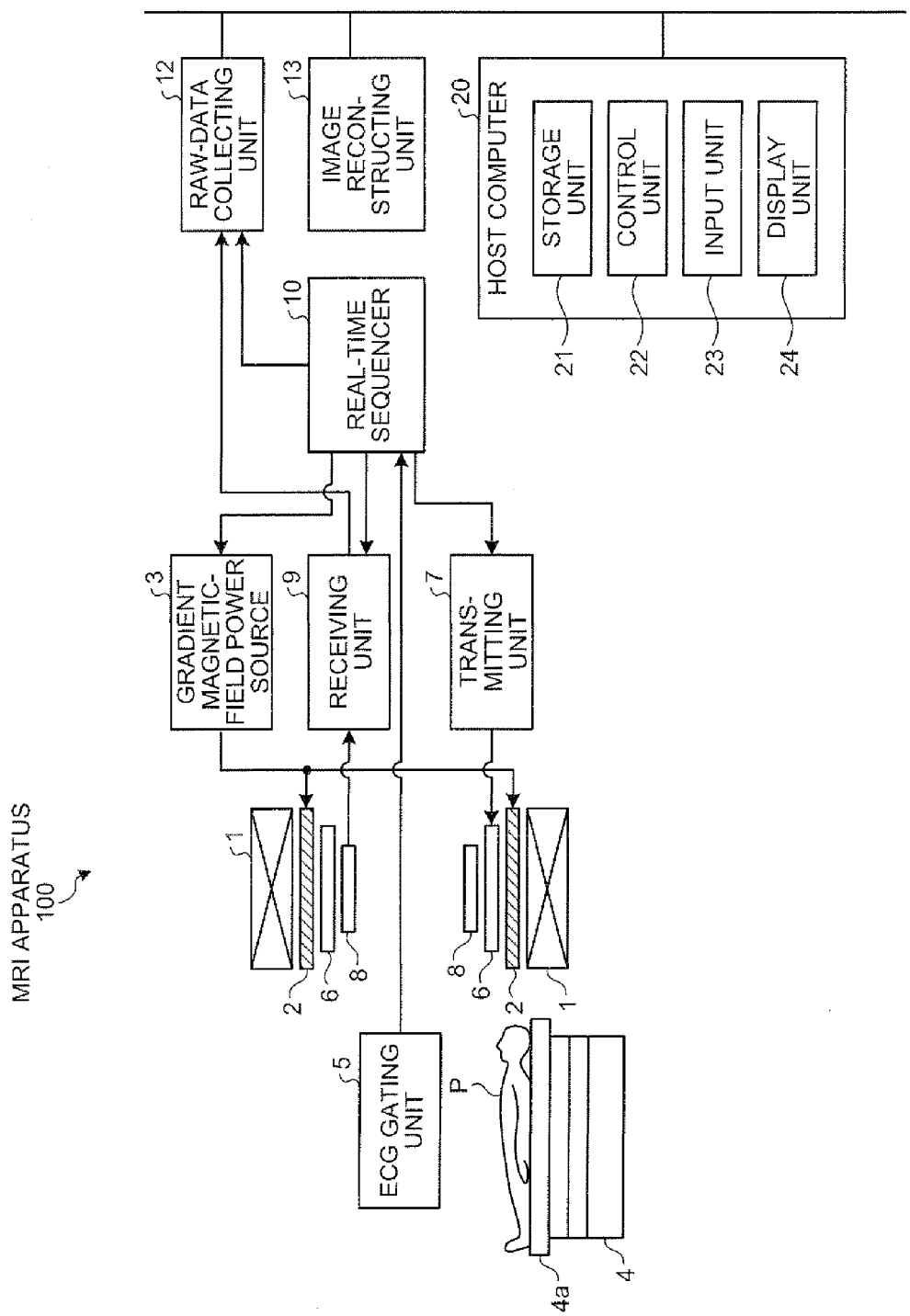
FIG. 15 is a functional block diagram of a configuration of an MRI apparatus according to a fourth embodiment of the present invention.

FIG. 15 is a functional block diagram of a configuration of an MRI apparatus according to the fourth embodiment. As shown in FIG. 15, the MRI apparatus 100 according to the fourth embodiment does not include the raw-data buffer substrate 11. Accordingly, when the receiving unit 9 according to the fourth embodiment creates raw data of received MRI echo signal, the receiving unit 9 directly transmits the created raw data to the raw-data collecting unit 12.

When receiving a notice of detection of a BAD beat from the ECG gating unit 5, similarly to the first to third embodiments, the real-time sequencer 10 according to the fourth embodiment transmits sequence information to the gradient magnetic-field power source 3, the transmitting unit 7, and the receiving unit 9 so as to reacquire raw data equivalent to data of which acquisition ends in failure; however, differently from the first to third embodiments, the real-time sequencer 10 directly notifies the raw-data collecting unit 12 that a BAD beat is detected.

Several methods are conceivable as processing to be performed by the raw-data collecting unit 12 at this stage, which has received a notice that a SAD beat is detected. For example, a conceivable method can be such that the raw-data collecting unit 12 attaches a tag. For example, the raw-data collecting unit 12 can be configured to attach a tag indicating raw data of which acquisition ends in failure (for example, "failure tag") onto raw data that is the subject of a notice when receiving the notice from the real-time sequencer 10. The image reconstructing unit 13 then excludes the raw data attached with the "failure tag" from subjects of the reconstruction processing, and performs the reconstruction processing after a required amount of raw data without attached "failure tag" are collected. The method can be arbitrarily changed to a method of attaching a "success tag" in addition to a "failure tag", a method of attaching only a "success tag" without attaching "failure tag", or the like.

Moreover, a method of controlling whether the raw-data collecting unit 12 transfers raw data to the image reconstructing unit 13 in the subsequent stage is conceivable. For example, the image reconstructing unit 13 can be configured to perform the reconstruction processing by using all raw data collected from the raw-data collecting unit 12 in the earlier stage. In such case, control can be provided such that when the raw-data collecting unit 12 receives a notice from the real-time sequencer 10, the raw-data collecting unit 12 does not transfer raw data that is the subject of the notice to the image reconstructing unit 13.

The methods described above according to the fourth embodiment (methods without the raw-data buffer substrate 11) can be similarly applied to the first to third embodiments. In other words, the methods according to the fourth embodiment can be similarly applied regardless of the method of reacquiring raw data of one heart-beat equivalent (the first and third embodiments), or the method of reacquiring raw data of a preset number of heart-beat equivalent (the second embodiment). Moreover, the methods according to the fourth embodiment can be similarly applied regardless of the imaging method of acquiring one MRI echo signal with respect to one heart beat (the first and second embodiments), or the imaging method of acquiring a plurality of MRI echo signals with respect to one heart beat (the third embodiment).

The first to fourth embodiments have been explained above, and moreover, the present invention can be implemented in various forms in addition to the above embodiments.

For example, the MRI apparatus can be configured such that the number of times of retry of imaging (for example, the maximum acceptable number of times) is preliminarily set, and when a retry of imaging occurs beyond the set number of times, information of advising the operator to stop imaging, or allowing the operator to pause imaging or to resume operation can be displayed on the display unit 24. This can be applied to the first to fourth embodiments.

For example, as shown in FIG. 16, the real-time sequencer 10 counts how many times detection of a BAD beat is received (Step S501), and determines whether the number of times the detection of a BAD beat is received exceeds five times (Step S502). If not exceeding five times (No at Step S502), the process control goes back to the processing of counting; by contrast, if exceeding five times (Yes at Step S502), the real-time sequencer 10 notifies so the host computer 20. The control unit 22 of the host computer 20 then displays on the display unit 24 information of advising the operator to stop imaging, or allowing the operator to pause imaging or to resume operation (Step S503). FIG. 16 is a flowchart of a process procedure performed by the real-time sequencer.

In such case, the MRI apparatus can improve convenience by including a configuration for leaving determination to the operator while implementing automatic recovery of raw data.

Moreover, according to the first to fourth embodiments, when it is notified from the ECG gating unit 5 that a BAD beat is detected, the real-time sequencer 10 returns back the pointer that manages the TR number of a sequence to be executed at present to one TR earlier, and immediately executes reacquisition of raw data equivalent to data of which acquisition ends in failure; however, the present invention is not limited to this. For example, reacquisition of raw data equivalent to data of which acquisition ends in failure can be performed after execution of a series of sequences is finished.

For example, in FIG. 7, it is assumed that the ECG gating unit 5 detects during a period between the heart beat 3 and the heart beat 4 that the interval between the heart beat 2 and the heart beat 3 is an irregular synchronization interval, and notifies the real-time sequencer 10 that a BAD beat is detected. The real-time sequencer 10 then stores, for example, a TR number of one TR earlier from the pointer that manages the TR number of a sequence to be executed at present as the TR number of a sequence to be reexecuted. For example, when the pointer is positioned at "TR 3" as the TR number of a sequence to be executed at present, the real-time sequencer 10 stores "TR 2", which is one TR earlier, as the TR number of a sequence to be reexecuted.

At this stage, differently from the first to fourth embodiments, the real-time sequencer 10 does not immediately execute "TR 2", but continuously executes a series of the sequences (for example, from "TR 3" to "TR 9"). After executing the series of the sequences, the real-time sequencer 10 transmits the sequence information about "TR 2", which is stored a short while ago, to the gradient magnetic-field power source 3, the transmitting unit 7, and the receiving unit 9 so as to execute the sequence of the "TR 2".

The method described above (method of performing reacquisition of raw data after execution of a series of sequences) can be similarly applied to the first to fourth embodiments. In other words, the method can be similarly applied regardless of the method of reacquiring raw data of one heart-beat equivalent (the first and third embodiments), or the method of reacquiring raw data of a preset number of heart-beat equivalent (the second embodiment). Moreover, the methods can be similarly applied regardless of the imaging method of acquiring one MRI echo signal with respect to one heart beat (the first and second embodiments), or the imaging method of acquiring a plurality of MRI echo signals with respect to one heart beat (the third embodiment). Furthermore, the method can be similarly applied regardless of the method with the raw-data buffer substrate 11 (the first to third embodiments) or the method without the raw-data buffer substrate 11 (the fourth embodiment).

The functional responsibilities of the raw-data buffer substrate 11 and the real-time sequencer 10 according to the above embodiments can be changed as required. For example, when the raw-data buffer substrate 11 is a simple volatile memory (without a logic gate unit), the real-time sequencer 10 can be configured to control transferring and not-transferring. For example, the raw-data buffer substrate 11 can be configured to receive a notice of detection of a BAD beat directly from the ECG gating unit 5.

As described above, the magnetic resonance imaging apparatus according to the exemplary embodiments is useful for imaging a subject and acquiring raw data, and is particularly suitable for reducing imaging time.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic resonance imaging (MRI) apparatus comprising:
    an electrocardiographic (ECG) signal detector configured to be coupled to a subject patient and to provide ECG signals used to determine patient heart beat intervals;
    an MRI gantry including a static magnet, gradient magnets, at least one radio-frequency (RF) coil coupled to RF transmitter and receiver circuits, a data collection memory, and control circuits connected to control use of such MRI gantry components, said control circuits including a data buffer connected to intermediate between the acquisition of raw MRI data and storage of the acquired data in the data collection memory including a region configured to buffer new data equivalent to that collected for a preset number of at least three heart beat intervals and at least one control computer configured to effect:
    acquisition of raw MRI data from a subject patient for a medical image into said data buffer by execution of a series of MRI data acquisition sequences synchronized with an electrocardiographic signal of the subject patient;
    detection of an irregular synchronization interval with respect to the electrocardiographic signal during execution of said series of sequences;
    transfer of acquired raw MRI data from the data buffer to the data collection memory where correction processing of therein accumulated raw MRI data is performed while further raw MRI data is still being acquired, unless an irregular synchronization interval is detected as possibly affecting the quality of the acquired data not yet transferred to said data collection memory, after buffering raw data from said preset number of heart beat intervals; and
    reacquisition of raw MRI data into said data buffer which corresponds to raw data not yet transferred to the data collection memory due to detection of an irregular synchronization interval, said reacquisition of raw MRI data being automatic and occurring before execution of said series of sequences for a complete medical image finishes, which reacquired raw data corresponds to raw data acquired during a period starting before and including the irregular synchronization interval.

2. The magnetic resonance imaging apparatus according to claim 1, wherein said control circuits are further configured to count a number of times of reacquisition, and when the counted number of times reaches a preset number, outputs to a user selection information that advises at least one of: (a) stop imaging and (b) retry imaging.

3. The MRI apparatus of claim 1 further comprising:
    a sequence information memory wherein MRI data acquisition sequence information is stored for each of plural repetition intervals (TR); and said at least one control computer is configured to sequentially effect acquisition of raw MRI data into said data buffer by executing pointer-designated ones of said TR sequences, a pointer being re-used to effect reacquisition of raw MRI data in response to detection of an irregular synchronization interval.

4. The MRI apparatus of claim 3 wherein said pointers constitute an ordered sequence which are, in the absence of a detected irregular synchronization interval, sequentially used in a predetermined order as determined by a pointer value, and wherein when an irregular synchronization interval is detected, the pointer value is immediately decremented back in the ordered sequence by a predetermined number of TR intervals equal to said preset number.

5. A magnetic resonance imaging (MRI) method comprising:

acquiring raw MRI data from a subject for a medical image into a data buffer which includes a region configured to buffer raw data equivalent to that collected for a preset number of at least three heart beat intervals by execution of a series of MRI data acquisition sequences in a synchronized manner with an electrocardiographic signal of the subject;

detecting an irregular synchronization interval with respect to the electrocardiographic signal during execution of said series of sequences;

transferring acquired raw MRI data from the data buffer to a data collection memory where correction processing of therein accumulated raw MRI data is performed while further raw MRI data is still being acquired, unless an irregular synchronization interval is detected as possibly affecting the quality of the acquired data, after buffering raw data from said preset number of heart beat intervals; and automatically selectively reacquiring raw MRI data from the subject into said data buffer, before execution of said series of sequences for a complete medical image finishes, said reacquired raw data corresponding to raw data acquired during a period starting before and including the irregular synchronization interval.

* * * * *